(12) United States Patent
Liphardt et al.

(10) Patent No.: US 6,930,813 B1
(45) Date of Patent: Aug. 16, 2005

(54) SPATIAL FILTER SOURCE BEAM CONDITIONING IN ELLIPSOMETER AND THE LIKE SYSTEMS

(75) Inventors: Martin M. Liphardt, Lincoln, NE (US); Blaine D. Johs, Lincoln, NE (US); Craig M. Herzinger, Lincoln, NE (US); Ping He, Lincoln, NE (US); James D. Welch, Omaha, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 114 days.

(21) Appl. No.: 10/425,801

(22) Filed: Apr. 29, 2003

Related U.S. Application Data

(63) Continuation-in-part of application No. 09/854,548, filed on May 14, 2001, now abandoned, and a continuation-in-part of application No. 09/840,483, filed on Apr. 23, 2001, now Pat. No. 6,590,655.

(60) Provisional application No. 60/207,537, filed on May 26, 2000, provisional application No. 60/201,847, filed on Apr. 25, 2000.

(51) Int. Cl.[7] ............................ G02F 1/00; G02F 1/33; G01J 4/00; G01J 3/28; G01J 3/50
(52) U.S. Cl. ...................... 359/237; 359/308; 359/641; 356/369; 356/327; 356/73; 356/445; 250/226; 250/227.15; 250/372; 73/657; 600/476
(58) Field of Search ................................ 359/237, 308, 359/558, 738, 740, 385, 618, 641; 356/73, 356/327, 369, 445, 448; 73/655, 657; 250/225, 250/226, 237, 372, 227.15; 600/476

(56) References Cited

U.S. PATENT DOCUMENTS

| | | | |
|---|---|---|---|
| 3,905,675 A | 9/1975 | McCracken | 350/17 |
| 4,522,466 A * | 6/1985 | Lindig et al. | 359/308 |
| 4,645,300 A * | 2/1987 | Brandstetter et al. | 359/285 |
| 4,877,960 A | 10/1989 | Messerschmidt et al. | 250/341 |
| 4,906,069 A * | 3/1990 | Brandstetter et al. | 359/285 |
| 4,996,120 A | 2/1991 | Smothers et al. | 430/2 |
| 5,032,734 A | 7/1991 | Orazio, Jr. et al. | 250/572 |
| 5,045,689 A * | 9/1991 | Froehly et al. | 250/227.15 |
| 5,148,323 A | 9/1992 | Campbell et al. | 359/738 |
| 5,159,412 A * | 10/1992 | Willenborg et al. | 356/445 |
| 5,414,559 A | 5/1995 | Burghardt et al. | 359/623 |
| 5,426,506 A | 6/1995 | Ellingson et al. | 356/369 |
| 5,517,312 A | 5/1996 | Finarov | 356/386 |
| 5,608,526 A | 3/1997 | Piwonka-Corle et al. | 356/369 |
| 5,684,642 A | 11/1997 | Zumoto et al. | 359/740 |
| 5,748,308 A * | 5/1998 | Lindberg et al. | 356/310 |
| 5,796,521 A | 8/1998 | Kahlert et al. | 359/619 |
| 5,859,424 A | 1/1999 | Norton et al. | 250/226 |
| 5,889,593 A | 3/1999 | Bareket | 356/445 |
| 5,910,842 A | 6/1999 | Piwonka-Corle et al. | 356/369 |
| 5,917,594 A | 6/1999 | Norton | 356/327 |
| 6,134,012 A | 10/2000 | Aspnes et al. | 356/369 |
| 6,184,984 B1 | 2/2001 | Lee et al. | 356/369 |

(Continued)

*Primary Examiner*—Loha Ben
(74) *Attorney, Agent, or Firm*—James D. Welch

(57) ABSTRACT

Disclosed is the application of spatial filters and beam energy homogenizing systems in ellipsometer and the like systems prior to a sample system. The purpose is to eliminate a radially outer annulus of a generally arbitrary intensity profile, so that electromagnetic beam intensity is caused to quickly decay to zero, rather than, for instance, demonstrate an irregular profile as a function of radius.

21 Claims, 7 Drawing Sheets

U.S. PATENT DOCUMENTS

| | | | |
|---|---|---|---|
| 6,256,097 B1 * | 7/2001 | Wagner | 356/369 |
| 6,321,601 B1 | 11/2001 | Maris | 73/657 |
| 6,456,376 B1 * | 9/2002 | Liphardt et al. | 356/369 |
| 6,798,511 B1 * | 9/2004 | Zhan et al. | 356/369 |
| 2001/0046089 A1 * | 11/2001 | Liphardt et al. | 359/618 |
| 2004/0133112 A1 * | 7/2004 | Rajadhyaksha | 600/476 |

* cited by examiner

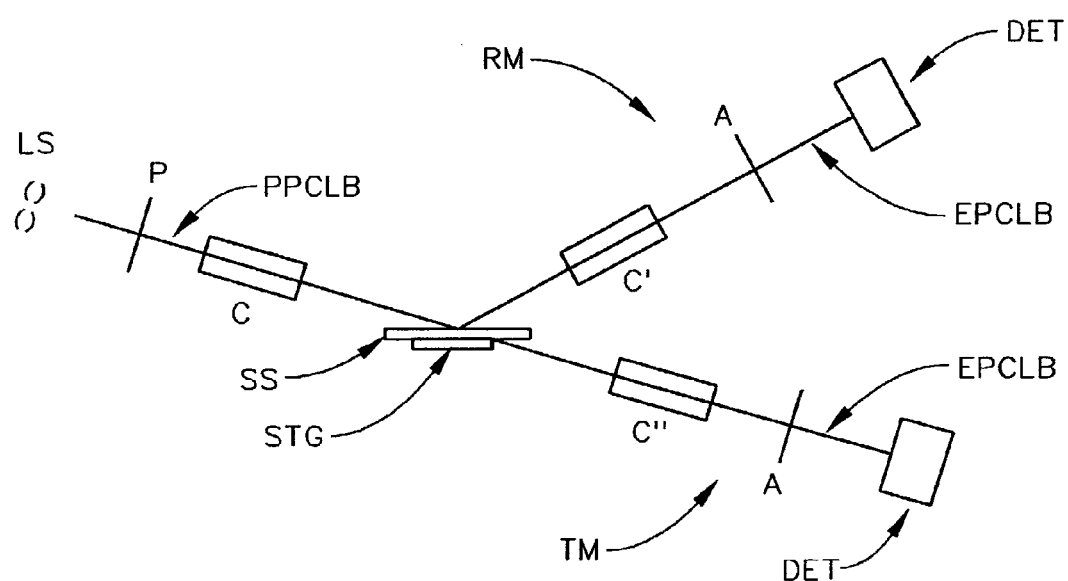
FIG. 1a₁
PRIOR ART

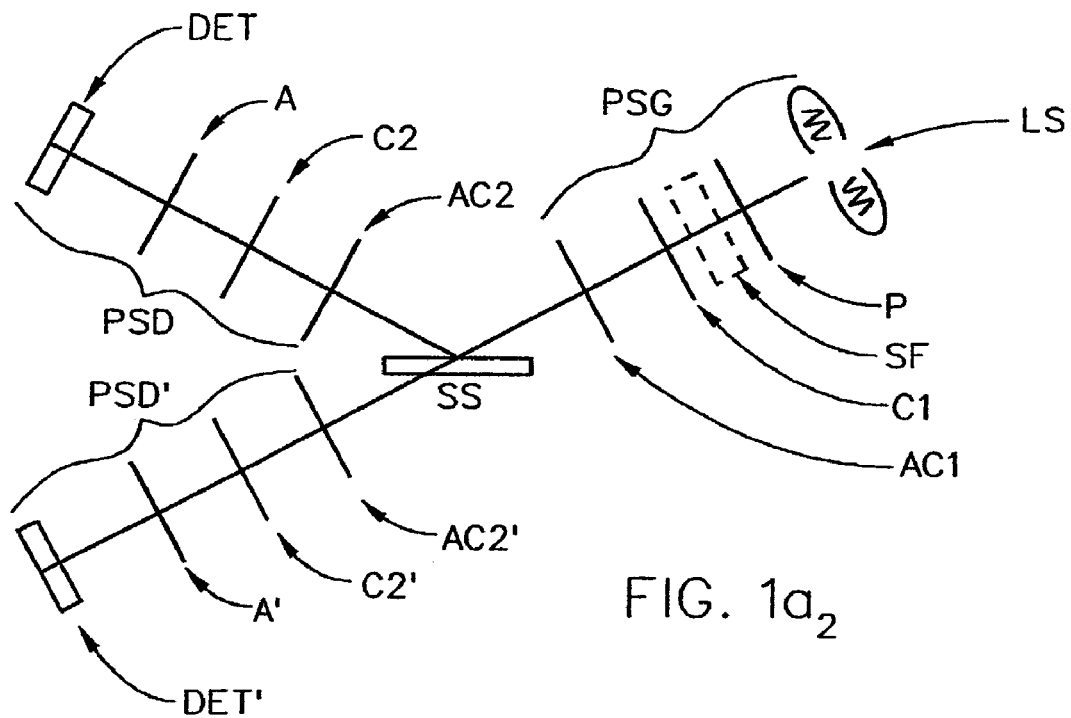
FIG. 1a₂
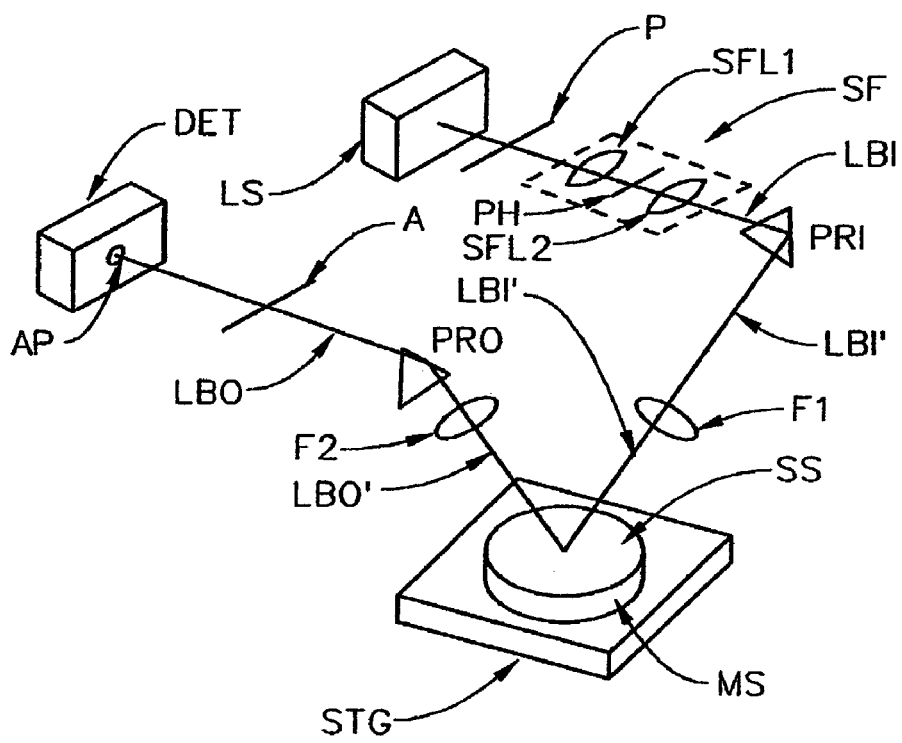
FIG. 1a₃

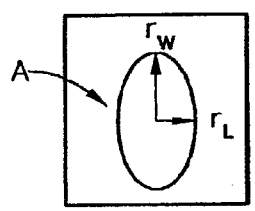
FIG. 7a
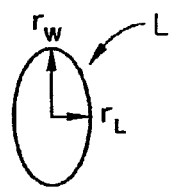
FIG. 7b
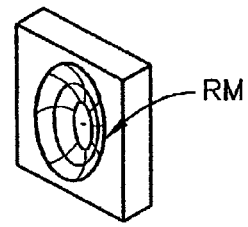
FIG. 7c₁
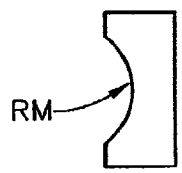
FIG. 7c₂
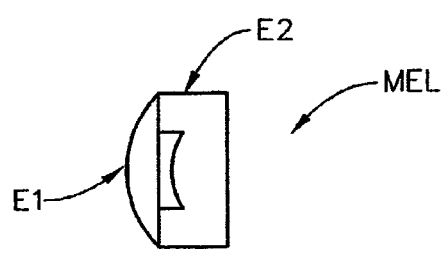
FIG. 7d
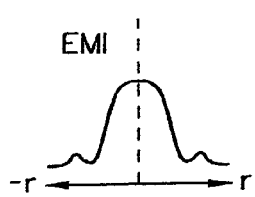
FIG. 8a
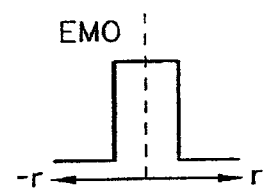
FIG. 8b₁
FIG. 8b₂
FIG. 8c

SPATIAL FILTER SOURCE BEAM CONDITIONING IN ELLIPSOMETER AND THE LIKE SYSTEMS

This Applications is claims priority from applications Ser. No. 09/854,548 Filed May 14, 2001 now abandon and application Ser. No. 09/840,483 Filed Apr. 23, 2001 U.S. Pat. No. 6,590,655; and claims Benefit of Provisional Application Ser. No. 60/207,537 filed May 26, 2000, and Ser. No. 60/201,847 Filed Apr. 25, 2000.

TECHNICAL FIELD

The present invention relates to systems and methods for processing electromagnetic beams and more particularly to application of beam energy homogenizing systems and spatial filters in ellipsometer and the like systems prior to investigated sample systems, which serve to eliminate a radially outer annulus in which intensity is comprised of undesirable irregular low intensity level content.

BACKGROUND

Not limited to, but particularly in the case where an electromagnetic beam is utilized to investigate a sample system which presents with a varying depth surface topology, it is important to provide an electromagnetic beam of a known lateral dimension and which presents with a relatively simple cross-sectional Intensity profile.

It is noted that often electromagnetic beams present with a substantially arbitrary intensity profile, with the highest intensity generally being located centrally, and with intensity decreasing with increasing radius. While such a beam intensity profile is typically acceptable for use in ellipsometry and related practices, it has been found that once the intensity of a substantially arbitrary profile beam of electromagnetic radiation has dropped to, as an arbitrary example, say ten (10%) of its maximum, that said intensity in many beams does not always continue to decay directly to essentially zero (0.0). Instead, it often presents irregularly as a function of radius, (eg. easily visualized as being generally similar to the Fourier transform of a square wave). The cause of said irregular intensity profile can include such as optical element wavelength dependent diffraction, surface roughness or other non-idealities, and where, for instance, electromagnetic radiation is provided via an aperture or via the end of a light fiber contained in a cladding, such that electromagnetic radiation falls outside a geometric image thereof.

It would be of benefit, as regards obtaining accurate data from application of ellipsometers and the like systems, if the intensity of an electromagnetic beam could be forced to decay quickly to zero (0.0), rather than demonstrate an irregular intensity profile as a function of radius.

With an eye to the present invention, a Search of Patents was conducted. With respect to the Spatial Filter aspect of the Disclosed Invention, perhaps the most relevant Patent identified is No. 5,517,312 to Finarov. Said 312 Patent describes application of a scattered light reducing system at the entry to a Detector of an Ellipsometer or Spectrophotometer System, which scattered light reducing system consists of two lenses with a pin-hole containing diaphram located midway therebetween, and at the focal lengths of said lenses. Said scattered light reducing system is present after a sample system and processes electromagnetic radiation after it interacts with said sample system. The pinhole is described as serving to provide high spatial resolution as well as reduce scattered light. Another Patent identified is that to Campbell et al., U.S. Pat. No. 5,148,323. Said 323 Patent describes a Spatial Filter in which a pinhole is located other than at the focal length of a converging lens. U.S. Pat. No. 3,905,675 to McCraken describes a Spatial Filter containing system which enables observation of a weak source of electromagnetic radiation in the presence of strong sources thereof. U.S. Pat. No. 5,684,642 to Zumoto et al., describes an optical transmission system for use in fashioning an electromagnetic beam for use in machining materials which combines a Spatial Filter and an Optical Fiber. U.S. Pat. No. 4,877,960 is identified as it describes masking energy from outside the target area of a in a microscope having dual remote image masking. U.S. Pat. No. 5,426,506 to Ellingson et al. is disclosed as it teaches a Spatial Filter after a reflecting means in an optical apparatus for detection of surface defects in dense ceramics. (Note that the disclosed inventions either has no reflecting means for directing an electromagnetic beam, or places a spatial filter before, not after, a reflecting means. U.S. Pat. No. 6,134,012 to Aspnes; U.S. Pat. No. 6,321,601 to Maris; and U.S. Pat. No. 4,996,120 to Smothers et al. are disclosed as they are known to the Applicant.

With respect to the Beam Energy Homogenization aspect of the Disclosed Invention, Patents disclosed are U.S. Pat. No. 5,608,526 to Piwonka-Corle et al. which describes application of optical elements with other than radial symetry in ellipsometer systems, however, typical application thereof is to enter compensation for various aberational effects. U.S. Pat. No. 5,859,424 to Norton et al. discloses use of an apodizing filter used to reduce spot size in optical measurements. Patent to Burghardt et al., U.S. Pat. No. 5,414,559 is disclosed as it describes a device for homogenizing a light beam. U.S. Pat. No. 5,796,521 to Kahlert et al. is disclosed as it describes optical apparatus for homogenizing electromagnetic beams which comprises cylindrical lenses.

Even in view of the known art, especially in the context of polarimeter, ellipsometer, reflectometer, spectrophotometer and the like systems, a need exists for a means to fashion a beam with a radially arbitrary intensity profile that does not quickly decay to zero, into a beam in which the energy intensity is relatively homogeneous radially and approaches zero intensity quickly beyond its extent.

DISCLOSURE OF THE INVENTION

The present invention comprises at least one Spatial Filter in the context of a system selected from the group:
 reflectometer;
 spectrophotometer;
 ellipsometer;
 spectroscopic ellipsometer;
 polarimeter; and
 spectroscopic polarimeter;
 and the like;

which system alone, or in combination with additional elements, generates an electromagnetic beam and causes it to impinge upon a sample system via said at least one spatial filter;

the purpose of said at least one spatial filter being to attenuate an outer annular region from said electromagnetic beam as it passes therethrough.

Spatial filters minimally sequentially comprise:
 beam converging at least one lens or mirror;

diaphram with a pin hole therein located near the focal length of said beam converging at least one lens or mirror; and beam collimating at least one lens or mirror;

such that in use an electromagnetic beam which is caused to interact with said beam converging at least one lens or mirror becomes focused on, and at least partially passes through said pin hole in said diaphram, and then becomes recollimated by said second beam at least one collimating lens or mirror. It should be appreciated, of course, that the beam converging or collimating at least one lens or mirror can comprise a system of a plurality of lenses or mirrors.

A preferred present invention system comprises addition of an aperture such that the configuration becomes:
   first beam collimating lens;
   at least one aperture;
   first beam converging at least one lens or mirror;
   diaphram with a pin hole therein located essentially at the focal length of said beam converging at least one lens or mirror; and
   second beam collimating at least one lens or mirror;

and such that, in use, the central portion of the electromagnetic beam which is collimated by said first beam collimating lens is caused to pass through said at least one aperture, become focused on and at least partially pass through said pin hole in said diaphram by said first beam converging at least one lens or mirror, and become recollimated by said second beam collimating at least one lens or mirror.

The present invention can also be considered to be a system which comprises:
   polarization state generator which functionally includes said spatial filter;
   means for supporting a sample system; and
   polarization state detector;

wherein the spatial filter sequentially comprises:
   first at least one lens or mirror;
   pin hole containing diaphram; and
   second at least one lens or mirror;

and wherein electromagnetic radiation preferably enters said spatial filter via a collimating lens and at least one aperture;

said pin hole containing diaphram being positioned near the focal points of said first and second at least one lens or mirror, such that a collimated electromagnetic beam enters said first at least one lens or mirror, is converged and at least partially passes through said pin hole, and is recollimated by said second at least one lens or mirror.

As insight to why the present invention pre-sample system positioned spatial filter works, it can be considered that the pin hole in the diaphram acts as an aperture at the location of an image of the end of a fiber optic, or source aperture, or other point source of a beam.

The present invention is further a method of processing electromagnetic beams to eliminate a radially outer annulus which is often comprised of low intensity level irregular content, said method comprising placing at least one spatial filter(s) such that said electromagnetic beam passes therethrough, each present spatial filter sequentially comprising:
   beam converging at least one lens or mirror;
   diaphram with a pin hole therein located near the focal length of said beam converging at least one lens or mirror; and
   beam collimating at least one lens or mirror;

wherein electromagnetic radiation enters said spatial filter via a at least one aperture. In use, an electromagnetic beam which is caused to pass through said at least one aperture, become substantially focused on, and at least partially pass through said pin hole in said diaphram by said beam converging at least one lens or mirror, and then become recollimated by said second beam collimating at least one lens or mirror.

Said present invention method can be recited as, in the context of a selection from the group:
   reflectometer;
   spectrophotometer;
   ellipsometer;
   spectroscopic ellipsometer;
   polarimeter;
   spectroscopic polarimeter;
   the like;

which alone or in combination with other elements causes a beam of electromagnetic radiation to interact with a sample system, comprising the steps of:
   a. providing a beam of electromagnetic radiation;
   b. providing a sample system;
   c. placing at least one spatial filter(s) in the pathway of said electromagnetic beam such that said electromagnetic beam passes therethrough prior to said electromagnetic beam being caused to interact with a sample system;

the purpose being to eliminate a radially outer annulus of said electromagnetic beam which is comprised of a low intensity level irregular content.

In very general terms the present invention is a system which generates an electromagnetic beam and causes it to impinge upon a sample system, said system comprising, prior to said sample system, at least one spatial filter which serves to attenuate an outer annular region from said electromagnetic beam as it passes therethrough.

Finally, it is directly stated that the disclosed invention is a system which generates an electromagnetic beam and causes it to impinge upon a sample system, said system comprising, prior to said sample system, at least one spatial filter which serves to attenuate an outer annular region from said electromagnetic beam as it passes therethrough, said system being further characterized by a selection from the group consisting of:
   a) said at least one spatial filter is positioned prior to a beam directing reflecting means for directing a beam of electromagnetic radiation which directs said electromagnetic beam toward said sample system; and
   b) there is no beam directing reflecting means for directing a beam of electromagnetic radiation present prior to said sample system which directs said electromagnetic beam toward said sample system.

Stated alternatively, said selections can be described as being from a group consisting of:
   a) said at least one spatial filter is positioned prior to a beam directing reflecting means for directing an electromagnetic beam, which reflecting means directs said electromagnetic beam toward said sample system along a pathway which is other than substantially direct from said source of a beam electromagnetic radiation to said sample system; and
   b) said system provides said electromagnetic beam to said sample system along a substantially direct pathway from said source of a beam electromagnetic radiation to said sample system.

In either of the arrangements, the present invention can further comprise, in functional combination with the Spatial Filter a means for effecting cross-sectional, essentially radially uniform energy density in electromagnetic beams, said means for effecting cross-sectional, essentially radially uniform energy density in electromagnetic beams comprising a sequential combination of:
  beam expander;
  first beam collimator;
  at least one multi-faceted optical element;
  beam condenser; and
  second beam collimator;

such that in use electromagnetic radiation of arbitrary cross-sectional radial energy density is provided by said source of electromagnetic radiation and is caused to pass through said spatial filter and means for effecting cross-sectional, essentially radially uniform energy density in electromagnetic beams such that a beam of substantially radially uniform energy density is output therefrom, is caused to interact with a sample system placed on said stage for supporting a sample system, and then enter said detector.

The present invention reflectometer, spectrophotometer, polarimeter or ellipsometer system can also comprise at least one selection from the group consisting of:
  lens which presents with non-radial symmetry;
  focusing mirror with non-radial symetry; and
  apertures with non-radial symetry:

positioned between said means for effecting cross-sectional, essentially radially uniform energy density in electromagnetic beams, and said stage for supporting a sample system; such that said beam of electromagnetic radiation which impinges on said sample system, first interacts therewith to the end that an essentially circular shaped spot is effected upon the surface of said sample system.

Additionally, the present invention system can comprise, a reflectometer, spectrophotometer, polarimeter or ellipsometer system for application in non-destructive investigation of sample systems which sequentially comprises a source of electromagnetic radiation, an optical element which demonstrates non-radial symetry, a stage for supporting a sample system, and a detector, such that a beam of electromagnetic radiation provided by said source of electromagnetic radiation is caused to interact with said optical element which demonstrates non-radial symetry and then impinge on a surface of a sample system placed on said stage for supporting a sample system, thereat forming an essentially circular spot, said beam of electromagnetic radiation then being caused to enter said detector. Said optical element can be a lens which presents with non-radial symmetry; a focusing mirror with non-radial symetry; and apertures with non-radial symetry.

The reflectometer, spectrophotometer, polarimeter or ellipsometer system can further comprise a polarizer between said means for effecting cross-sectional, essentially radially uniform energy density in electromagnetic beams, and said stage for supporting a sample system, the purpose thereof being to cause a state of polarization on a beam of electromagnetic radiation caused to pass therethrough. Further, where a polarizer is included, an analyzer is typically included between the stage for supporting a sample system and the detector.

A present invention method of non-destructively analyzing a sample system in a reflectometer, spectrophotometer, polarimeter or ellipsometer system comprises:
  a. providing a reflectometer, spectrophotometer, polarimeter or ellipsometer system as described;
  b. placing a sample system on said stage for supporting a sample system;
  c. causing said source of electromagnetic radiation to perform at least one selection from the group:
    a. provide a beam of electromagnetic radiation of arbitrary cross-sectional radial energy density and causing it to pass through said means for effecting cross-sectional, essentially radially uniform energy density in electromagnetic beams such that a beam of substantially radially uniform energy density is output therefrom, is caused to impinge at an oblique angle upon, and interact with a sample system placed on said stage for supporting a sample system, and then enter said detector; or
    b. provide a beam of electromagnetic radiation provided by said source of electromagnetic radiation is caused to interact with optical element(s) which demonstrates non-radial symetry and then impinge on a surface of a sample system placed on said stage for supporting a sample system, thereat forming an essentially circular spot, said beam of electromagnetic radiation then being caused to enter said detector, said optical element(s) being a lens which presents with non-radial symmetry and/or a focusing mirror with non-radial symetry and/or apertures with non-radial symetry;
  said method optionally functionally combining a spatial filter along with said means for effecting cross-sectional, essentially radially uniform energy density in electromagnetic beams such that a beam of substantially radially uniform energy density is output therefrom.

It is emphasized that the disclosed invention can be practiced in the context of reflectometer, spectrophotometer, polarimeter or ellipsometer systems. Typically, reflectometers and spectrophotometers are distinguished from ellipsometers and polarimeters in that they lack polarization effecting and/or detecting means such as, respectfully, Polarizer and Analyzer means. Further, while reflectometers utilize unpolarized electromagnetic beams oriented to impinge on, and reflect from, a sample system surface at a close to normal angle of incidence, spectrophotmeters utilize electromagnetic beams oriented at any angle to the surface of a sample system, and can involve detection of reflected or transmitted beams.

The present invention will be better understood by reference to the Detailed Description Section of this Specification, in conjunction with the Drawings.

SUMMARY OF THE INVENTION

It is a purpose and/or objective of the present invention to teach positioning, prior to an investigated sample system, of a system for forming a beam of electromagnetic radiation which presents with an intensity profile which drops off radially quickly to 0.0, in reflectometer, ellipsometer, spectroscopic ellipsometer, polarimeter, spectroscopic polarimeter, spectrophotometer and the like systems.

It is a specific purpose and/or objective of the present invention to teach positioning, prior to an investigated sample system, of at least one spatial filter for forming a beam of electromagnetic radiation which presents with an intensity profile which drops off radially quickly to 0.0, in reflectometer, ellipsometer, spectroscopic ellipsometer, polarimeter, spectroscopic polarimeter, spectrophotometer and the like systems, said at least one spatial filter being characterized by a selection from the group consisting of:
  a) said at least one spatial filter is positioned prior to a beam directing reflecting means for directing an electromagnetic beam, which reflecting means directs said electromagnetic beam toward said sample system along a pathway which is other than substantially direct from said source of a beam electromagnetic radiation to said sample system; and b) said system provides said electromagnetic beam to said sample system along a substantially direct pathway from said source of a beam electromagnetic radiation to said sample system.

It is a specific purpose and/or objective of the present invention to teach a method for forming a beam of electromagnetic radiation which presents with an intensity profile which drops off radially quickly to 0.0, in reflectometer, ellipsometer, spectroscopic ellipsometer, polarimeter, spectroscopic polarimeter, spectrophotometer and the like systems.

It is another objective and/or purpose of the present invention to teach, in the context of reflectometer, spectrophotometer, polarimeter, ellipsometer and the like systems, application of means for effecting cross-sectional, essentially radially uniform energy density in electromagnetic beams.

It is yet another objective and/or purpose of the present invention to teach, in the context of reflectometer, spectrophotometer, polarimeter, ellipsometer and the like systems, application of optical element(s) which demonstrate non-radial symetry, for the purpose of causing a beam of electromagnetic radiation to form an essentially circular shaped spot upon the surface of a sample system, whereupon it impinges.

It is another objective and/or purpose yet of the present invention to teach, in the context of reflectometer, spectrophotometer, polarimeter, ellipsometer and the like systems, application of means for effecting cross-sectional, essentially radially uniform energy density in electromagnetic beams, in functional combination with spatial filters and optionally in functional combination with application of optical element(s) which demonstrates non-radial symmetry, for the purpose of causing a beam of electromagnetic radiation to form an essentially circular shaped spot upon the surface of a sample system, whereupon it impinges.

Other purposes and/or objectives of the present invention will become apparent by a reading of the Specification and claims.

BRIEF DESCRIPTION OF THE DRAWINGS

FIG. 1a1 shows a basic Reflectometer or Spectrophotometer comprising a Source of Electromagnetic Radiation and a Detector.

FIGS. 1a2, and 1a3 show demonstrative Ellipsometer systems in which the present invention spatial filter system is shown positioned prior to a sample system.

FIG. 2 shows an example of a source of electromagnetic radiation comprising a light fiber, lens, apertures and polarizer.

FIG. 7a demonstrates a non-circular aperture with a "width-wise" radius being larger than a "length-wise" radius.

FIG. 7b demonstrates a lens (L) with non-radial symetry.

FIG. 7c1 demonstrates, in perspective, a Reflective Mirror (RM) with non-radial symetry.

FIG. 7c2 shows said Reflective Mirror (RM) of FIG. 3c1 in side cross-sectional.

FIG. 7d is included to indicate that lens can be comprised of multi-elements.

FIG. 8a shows an arbitrary radial energy density Electromagnetic Beam profile present at Point "A" in FIG. 6, as provided by a typical Source of Electromagnetic Radiation (LS).

FIG. 8b1 shows an Essentially Uniform Radial Energy Density Electromagnetic Beam Profile which appears at Point "B" in FIG. 6.

FIG. 8b2 demonstrates that the Essentially Uniform Radial Energy Density Electromagnetic Beam at said Point "B" in FIG. 6 is of essentially circular cross-sectional dimensions.

FIG. 8c demonstrates that the Electromagnetic Beam Profile which appears at Point "C" in FIG. 6, after passing through the Optical Element (OL), with non-radial symetry is of an elliptical-like shape in cross-section.

DETAILED DESCRIPTION

Turning now to the Drawings, there is shown in FIG. 1a1 a basic Reflection and Transmission Ellipsometer or Polarimeter comprising a Source (LS) of Electromagnetic Radiation, a Polarizer (P) for setting a polarization State, Reflection and Transmission Analyzers (A) for monitoring a Polarization State, and a Detectors (DET). Also shown are Compensators which can be present and applied to further alter polarization state. Note if the Polarizer (P), Analyzer (A) and Compensators (C) (C') (C") are removed than the system becomes representative of a Reflectometer or Spectrophotometer. A Polarized Source Beam (PPCLB) beam of electromagnetic radiation is shown after reflecting from a Sample System (SS) and passing through the Analyzer (A) as (EPCLB).

Figure 2:
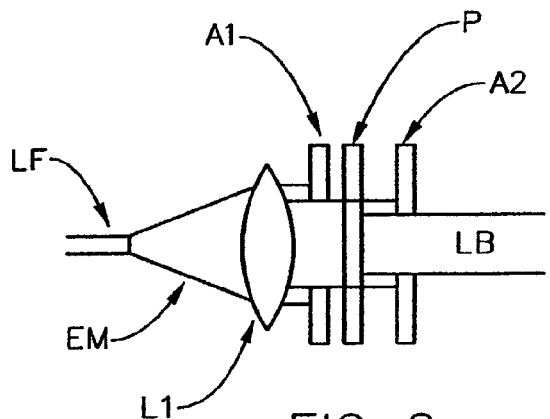

FIG. 1a2 shows a general elemental configuration of an ellipsometer system, (which can be a polarimeter if a compensator is present), to which the present invention can be applied to investigate a sample system (SS). Shown for reflection and transmission are:

a. a Source of a beam electromagnetic radiation (LS);
b. a Polarizer element (P);
c. optionally a compensator element (C1);
d. optional additional element(s) (AC1);
e. a sample system (SS);
f. optional additional element(s) (AC2);

g. optionally a compensator element (C2);
h. an Analyzer element (A); and
i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. optional "additional elements", (AC1) and (AC2), can be considered as being, for instance, optional input and output lenses or perhaps windows in a vacuum chamber.

Also note that after the Polarizer (P) there is indicated, in dashed lines, the presence of a present invention Spatial Filter (SF). While other pre-sample system locations, (eg. prior to the Polarizer (P), after the Compensator (C1) or after the Additional Elements (AC1), are included in the scope of the invention, the shown location is preferred.

Figure 3A:
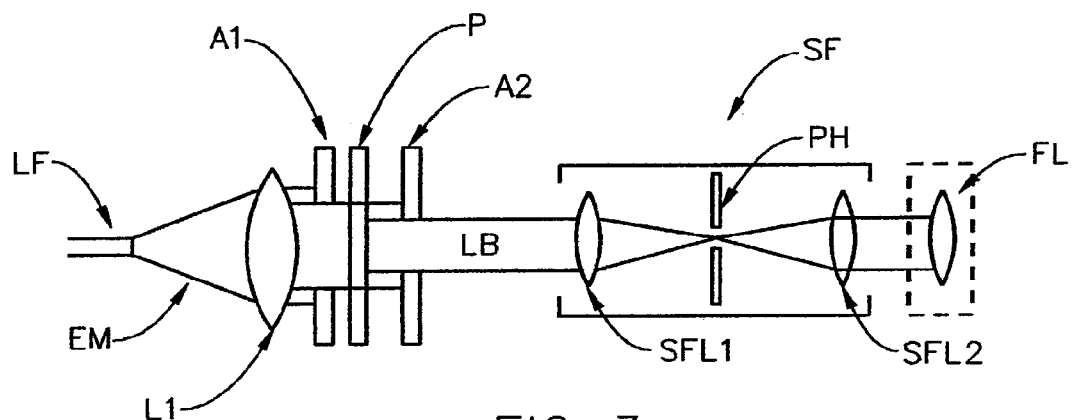
FIG. 3a shows an example of a present invention spatial filter in combination with the system of FIG. 2.
Figure 3B:
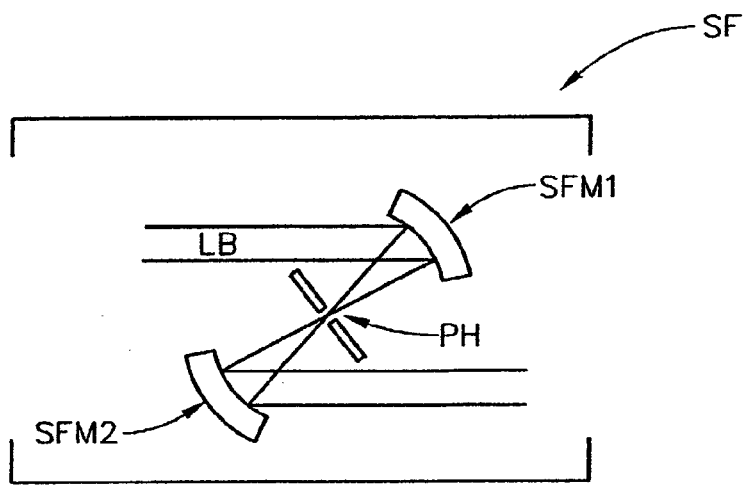
FIG. 3b shows alternative spatial filter construction which can be applied in the context of a FIG. 2 system.

Also shown in FIG. $1a_2$ is a present invention application of a Spatial Filter (SF), said Spatial Filter (SF) being shown and better presented and described with respect to FIGS. 3a and 3b.

Another embodiment of an ellipsometer system to which the present invention can be applied is shown in FIG. $1a3$, which shows a Perspective view of a demonstrative system. FIG. $1a3$ shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Sample System (SS), which can be any Material System (MS), present on a Material System supporting Stage (STG). FIG. $1a3$ shows that said interaction with the Surface of said Sample System (SS) causes a generally vertically oriented Polarized Beam of Electromagnetic Radiation (LBO') to pass through Focusing Optic (F2). FIG. $1a3$ also shows that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), preferably via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Sample System (SS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

Also, as in the FIG. $1a2$ case, note that shown after the Polarizer (P) there is indicated, in dashed lines, the presence of a present invention Spatial Filter (SF). Shown are a diaphram which contains a Pin Hole (PH), (which electromagnetic beam (LB1) passes through), which Pin Hole (PH) is located at essentially a Focal Length distant from each of Lenses (SFL1) and (SFL2). Again, while other pre-sample system locations are included in the scope of the invention, the shown location is preferred. Note that either of said Lenses (SFL1) and (SFL2) can be replaced with a functionally essentially equivalent mirror.

It is specifically pointed out that FIGS. $1a_2$ and $1a_3$, respectively, show a system comprising a spatial filter (SF) which either has no reflecting means, (see (PRI) in FIG. $1a_3$ as an example of a reflecting means), for directing an electromagnetic beam; or has a reflecting means (PRI) for directing an electromagnetic beam present after a spatial filter (SF). Further, while the Reflective Means (PRI) is demonstrated as a Totally Internally Reflecting Prism in FIG. $1a_3$, it is to be understood that it can be any functional means for reflecting electromagnetic radiation, such as a mirror. Stated alternatively, in FIG. $1a_2$ said system provides said electromagnetic beam to said sample system (SS) along a substantially direct pathway from said source (LS) of a beam electromagnetic radiation to said sample system (SS); and in FIG. $1a_3$ said at least one spatial filter (SF) is positioned prior to a beam directing reflecting means (PRI) for directing an electromagnetic beam, which reflecting means (PRI) directs said electromagnetic beam toward said sample system (SS) along a pathway which is other than substantially direct from said source (LS) of a beam electromagnetic radiation to said sample system (SS).

FIG. 2 shows that a Light Source (LS) can comprise a Light Fiber, a Lens (L1), and a First Aperture (A1). In the context of an ellipsometer a Polarizer (P) is also shown as it would be positioned. Shown in addition is a second Aperture (A2). In use electromagnetic radiation (EM) exiting the Light Fiber (LF) expands and enters Lens (L1) and is collimated thereby. First Aperture (A1) limits the beam diameter, and Second Aperture (A2) further does so to provide a beam of electromagnetic radiation labeled (LB).

FIG. 3a expands on FIG. 2 and shows a present invention spatial filter configuration. The Spatial Filter (SF) is placed so as to intercept the beam of electromagnetic radiation labeled (LB), and is converged by Lens or mirror (SFL1) such that it at least partially passes through a pin hole (PH) in a pin hole containing diaphram, (the diameter of which pin hole (PH) is typically about half that of the Light Fiber (LF) and corresponds to the Image diameter of the Light Fiber (LF) at the location of said Pin Hole (PH)), and then is re-collimated by Lens or mirror (SFL2). Note that The Pin Hole (PH) diameter, however, is not critical and can be bigger, and definitely smaller than just indicated. Also, the Pin Hole (PH) is generally located a Focal Length distant from each of the Lenses (SFL1) and (SFL2). Again it is to be understood that either of the Lenses (SFL1) and (SFL2) can be replaced by an essentially functionally equivalent mirror.

FIG. 3a also shows, (contained within dashed lines), that a Focusing Lens (FL) can also be present, and when present is functionally much like the Lens labeled (F1) in FIG. $1a_3$.

FIG. 3b shows alternative present invention Spatial Filter (SF) construction in which mirrors (SFM1) and (SFM2) perform the function of lenses (SFL1) and (SFL2) in FIG. 3a. That is the Spatial Filter shown in FIG. 3a can be replaced with that in FIG. 3b and remain within the scope of the present invention. It is further noted that a present invention Spatial Filter could comprise one Lens and one Mirror, in either order in a Spatial Filter, hence the language "lens or mirror" is to be interpreted broadly as meaning that each is independently selected from the group consisting of a lens and a mirror.

Figure 4:
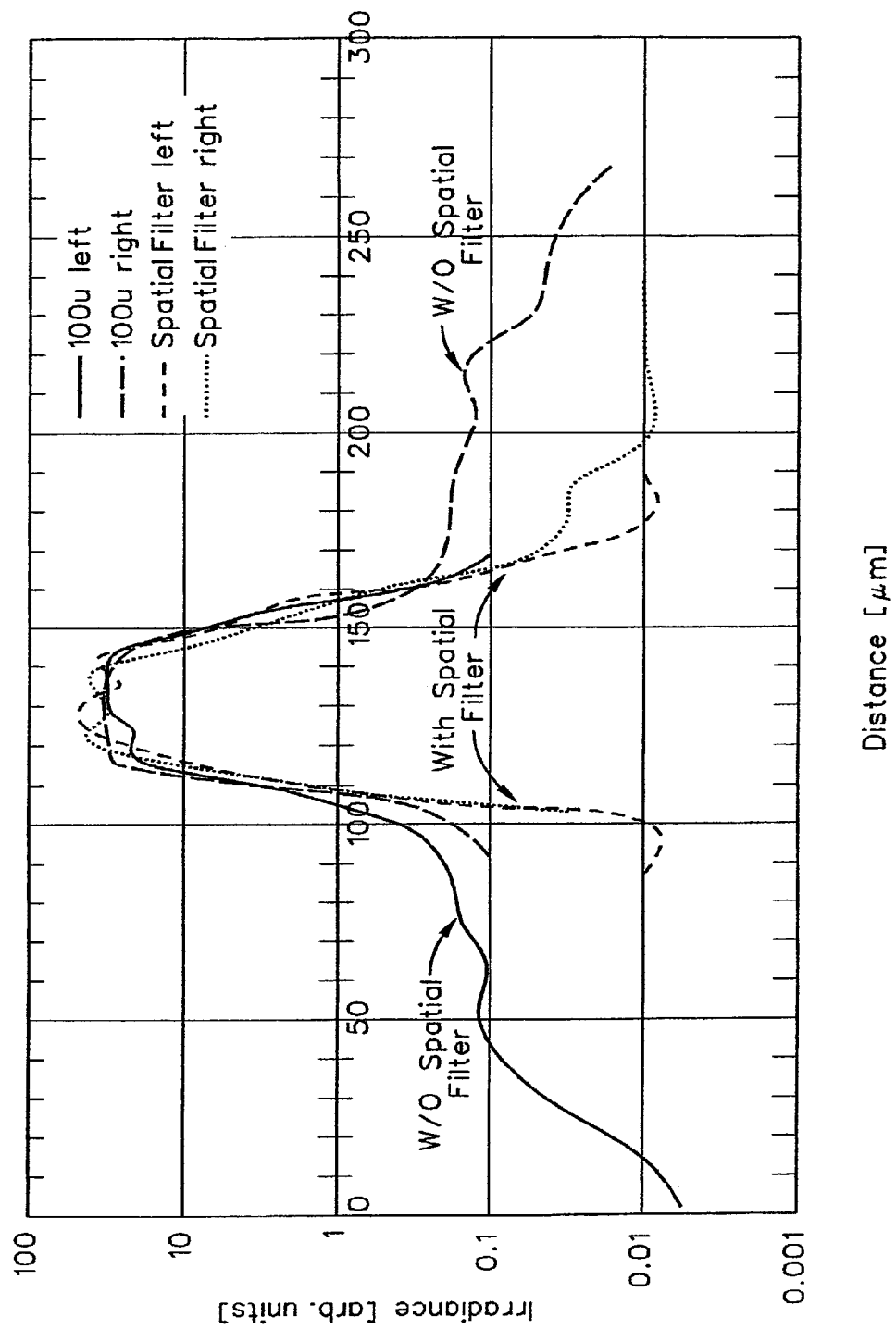
FIG. 4 shows the effect of the presence of a spatial filter on the radial intensity of an electromagnetic beam as is developed and utilized in ellipsometer, reflectometer and spectrophotometer etc. systems.

FIG. 4 shows the effect of the presence of the Spatial Filter (SF) as shown in FIG. 3a on the Intensity Profile of a beam of electromagnetic radiation passed therethrough. Note that FIG. 4 plots Intensity on a Log Axis, and that the Intensity drops toward 0.001 much quicker when the Spatial Filter (SF) is in place than when it is not in place.

Figure 5A:
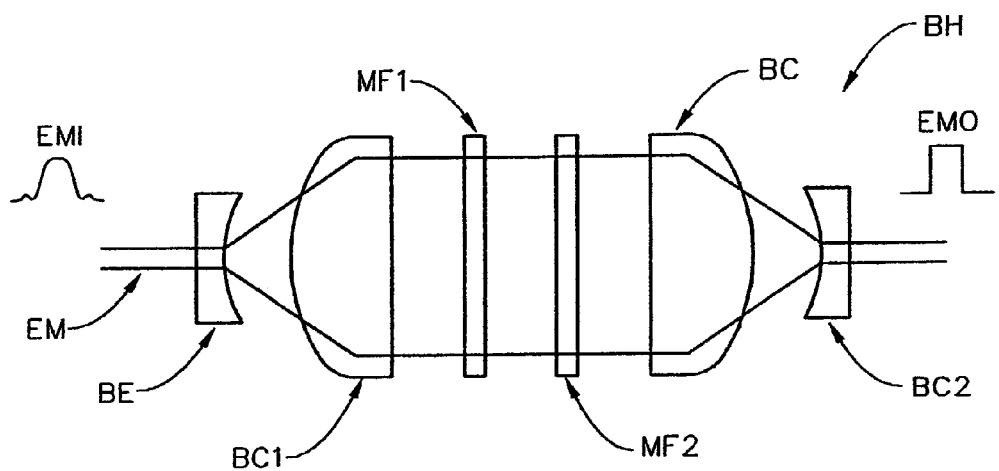
FIG. 5a shows a Beam Energy Homogenizing System means (BH) for effecting cross-sectional, essentially radially uniform energy density in electromagnetic beams.

FIG. 5a shows a Beam Energy Homogenizing means (BH) for effecting cross-sectional, essentially radially uniform energy density in electromagnetic beams. Shown a sequential combination of:

Beam Expander (BE);
First Beam Collimator (BC1);
at least one Multi-Faceted Optical Element (MF1) (MF2);
Beam Condenser (BC); and
Second Beam Collimator (BC2).

Figure 5B:
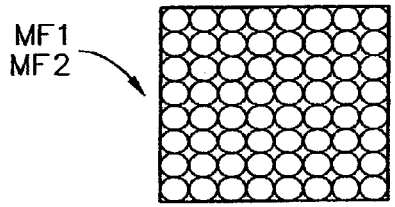
FIG. 5b demonstrates, in frontal view, that the at least one Multi-Faceted Optical Element(s) shown in side view in FIG. 5a, can comprise a lens with a multiplicity of small lenses distributed therewithin.
Figure 5C:
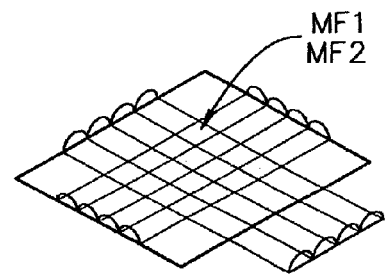
FIG. 5c shows in perspective that such Multi-Faceted Optical Element(s) can be fabricated as constructed from a plurality of half circular, (in cross-section), FIG. 6 demonstrates a present invention reflectometer, spectrophotometer, polarimeter or ellipsometer system comprising a combination Spatial Filter and Beam Energy Homogenizing Means (SFBH).

The effect of passing a Beam of Electromagnetic Radiation (EM) of arbitrary input radial Energy Density (EM1) is to produce a more uniform radial Energy Density (EMO) as output. FIG. 5b demonstrates, in frontal view, that the at least one Multi-Faceted Optical Element(s) (MF1) (MF2) shown in side view in FIG. 5a, can comprise a lens with a multiplicity of small lenses distributed therewithin. FIG. 5c shows in perspective that such Multi-Faceted Optical Element(s) (MF1) (MF2) can be fabricated as constructed from a plurality of half circular, (in cross-section), longitudinal elements aligned parallel to one another; directly adjacent to a second plurality of half circular, (in cross-section), longitudinal elements aligned parallel to one another, wherein the longitudinal orientations of the first and second plurality of half circular, (in cross-section), longitudinal elements are oriented other than parallel, (eg. at an angle of 90 degrees), to one another. (Note, the longitudinal elements need not be strictly half circular in cross-section, but can include half elliptical etc.).

In use the Multi-Faceted Optical Element(s) (MF1) (MF2) produce a multiplicity of images, each thereof being a portion of an Electromagnetic Beam (EM) which presents with energy density (EMI) produced by the Beam Expander (BE). The Beam Condensor (BC) then superimposes said multiplicity of images into a focused small area, which focused small area is collimated by Second Beam Collimator (BC2) into Output Electromagnetic Beam (EMO), which Output Electromagnetic Beam has a more radially uniform energy density (EMO) distribution than did the input Electromagnetic Beam (EMI).

Figure 6:
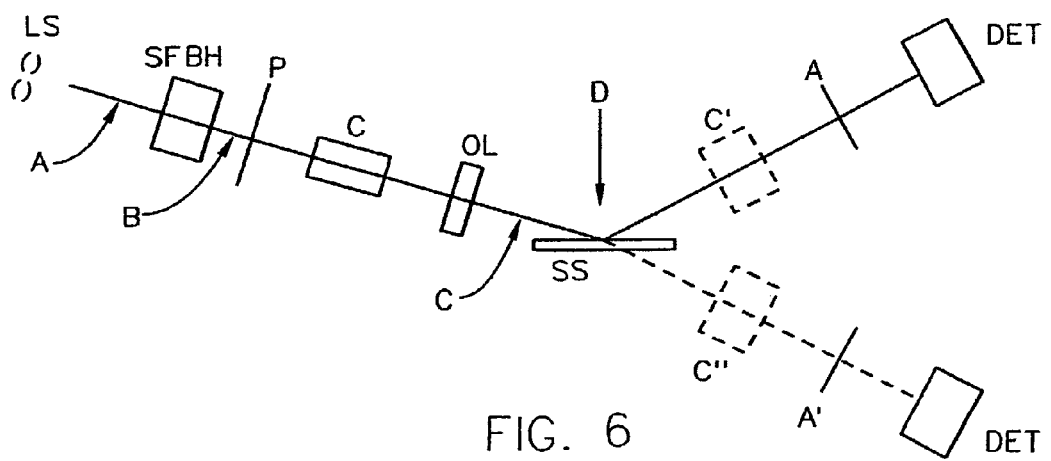

FIG. 6 demonstrates a present invention polarimeter or ellipsometer system much like that of FIG. 1a2 comprising a Source of electromagnetic Radiation (LS) and a combination Spatial Filter and Beam Energy Homogenizing Means (SFBH) for effecting cross-sectional, essentially radially uniform energy density in electromagnetic beams. Note that the Spatial Filter and Beam Energy Homogenizer System can be in either order and that (SFBH) could be termed (BHSF) with equal accuracy. Note that a beam of electromagnetic radiation at the location identified as "A" in FIG. 6 will have an Intensity Profile like (EMI) in FIG. 5a and that the Intensity Profile will appear as the FIG. 5a (EMO) at the location identified as "B". (See also the discussion regarding FIGS. 8a and 8b1). Also shown are Polarizer (P), Analyzer (A) for both Reflection and Transmission, Optical Element (OL) which can be applied to shape a Spot at location "D" on the Sample System (SS), and Reflection and Transmission Detectors (DET). The location "C" is identified as the Beam Shape thereat can be modified by Optical Element (OL) to be other than Circular, so that when said Beam impinges at "D" on the Sample System (SS) the Spot shape is Circular. With that in mind, it is noted that said optical element (OL) can be a lens which presents with non-radial symmetry; a focusing mirror with non-radial symetry; and apertures with non-radial symetry.

Note that Compensators (C) (C') (C") are also shown in the FIG. 6 System and can be applied to alter polarization state of a beam of electromagnetic radiation passing therethrough. Note also that where Polarizer (P), Analyzer (A) and Compensators (C) (C') (C") are removed, FIG. 6 represents a Reflectometer or Transmission Spectrophotometer.

Note that while not specifically shown, a Spatial Filter/Beam Energy Homogenizer System (SFBH) with the Spatial Filter and Beam Energy Homogenizer System in either order can also be in a System as shown in FIG. $1a_3$ and such is to be considered within the scope of the claims.

The present invention also includes, in the context of a reflectometer, a spectrophotometer, an ellipsometer, a spectroscopic ellipsometer, a polarimeter, a spectroscopic polarimeter, and a spectrophotometer and the like systems, the Method of removing an radial outer annular ring from an electromagnetic beam by application of a spatial filter and/or beam energy homogenizer system prior to a Sample System. Said method can be recited as a method of processing source electromagnetic beams to eliminate a radially outer annulus thereof, said radial outer annulus often being comprised of low intensity level irregular content, said method comprising placing at least one spatial filter(s) such that said electromagnetic beam passes therethrough. Said method can include that application of a beam energy homogenizing system (BH) as demonstrated in FIG. 5a in functional combination with the Spatial Filter (SF). When this is done, it is to be understood that a Polarization State Generating means (eg. a Polarizer (P) perhaps in combination with a Compensator (C)), must be present after the Beam Energy Homogenizing System/Spatial Filter (SFBH) functional combination, as the procedure of beam energy homogenization destroys a previously imposed polarization state. Note, where a Spatial Filter (SF) without energy homogenization capability is applied, the Polarization State Generating means (eg. a Polarizer (P) perhaps in combination with a Compensator (C)), can be placed ahead thereof, and preferred practice provides that it is, as shown in FIGS. $1a_2$ and $1a_3$.

Figure 9:
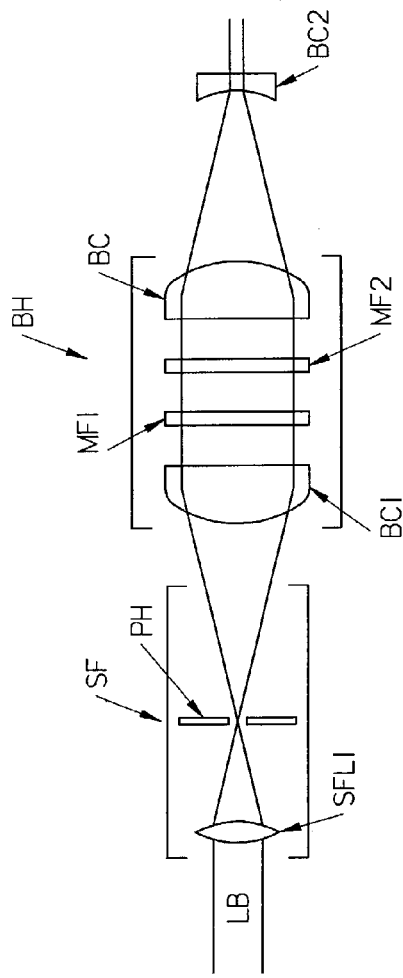
FIGS. 9 and 10 show specific non-limiting demonstrative combinations (SFBH) of Spatial Filters and Beam Energy Homogenizer Systems.
Figure 10:
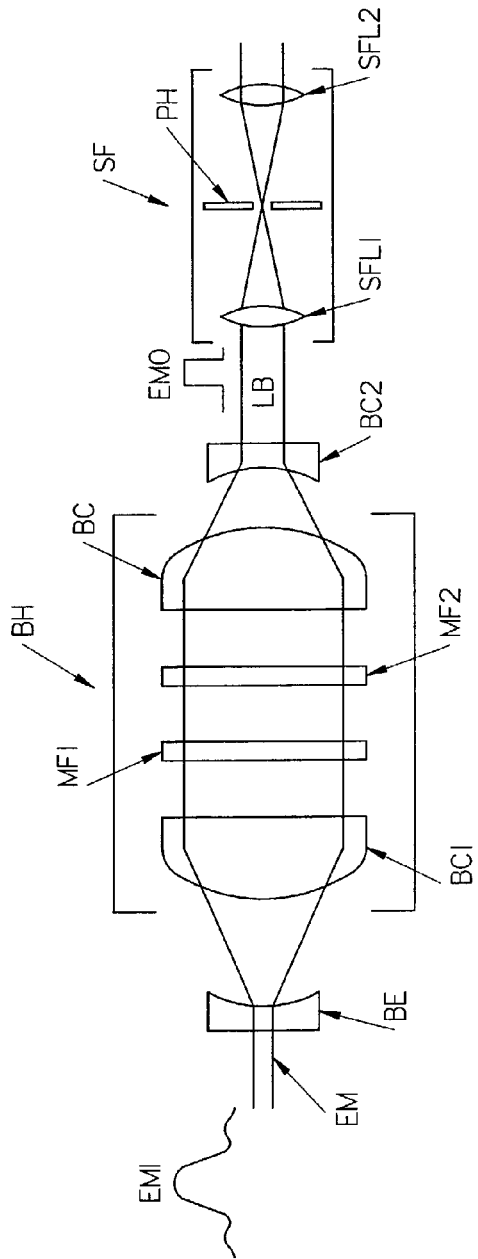

It is to be appreciated that where a functionally combined Spatial Filter/Beam Energy Homogenizing System (SFBH) is applied with the Spatial Filter (SF) being sequentially first, that the element (SFL2) in FIG. 3a can be the same as Beam Collimating element (BC1) in FIG. 5a, and that the Beam Expander (BE) in FIG. 5a can be eliminated, hence the Beam Expander (BE) is an optional element in the described functionally combined Spatial Filter/Beam Energy Homogenizing System (SFBH). Where the Beam Energy Homogenizing System is positioned sequentially first in the (SFBH), it is noted that the element (SFL2) in FIG. 3a can be the same as Beam Collimating element (BC) in FIG. 5a. (See FIGS. 9 and 10 for demonstrative non-limiting examples of combination (SFBH) Spatial Filter (SH) and Beam Energy Homogenizing Systems (BH)).

FIGS. 7a–7d demonstrate Optical Elements (OL), as identified in FIG. 6 as being optionally present, with non-radial symetry. Placing such an Optical Element (OL) so that it interacts with a cross-sectional circular shaped Beam of Electromagnetic Radiation prior to the Sample System (SS) causes it to assume an essentially cross-sectional elliptical shaped Beam of Electromagnetic Radiation. FIG. 7a demonstrates a non-circular aperture with a "width-wise" radius $(r_w)$ being larger than a "length-wise" $(r_l)$ radius. FIG. 7b demonstrates a lens (L) with non-radial symetry and FIG. 7c1 demonstrates, in perspective, a Reflective Mirror (RM) with non-radial symetry, and FIG. 7c2 shows said Reflective Mirror (RM) of FIG. 7c1 in side cross-sectional. FIG. 7d is included to indicate that lens can be comprised of multi-elements. Multi-element lenses can be of benefit where it is desired to achieve quasi-achromatic characteristics.

FIG. 8a shows an arbitrary radial energy density Electromagnetic Beam profile present at Point "A" in FIG. 6, as provided by a typical Source of Electromagnetic Radiation (LS).

FIG. 8b1 shows an Essentially Uniform Radial Energy Density Electromagnetic Beam Profile which appears at Point "B" in FIG. 6. FIG. 8b2 demonstrates that the Essentially Uniform Radial Energy Density Electromagnetic Beam at said Point "B" in FIG. 6 is of essentially circular cross-sectional dimensions. FIG. 8c demonstrates that the Electromagnetic Beam Profile which appears at Point "C" in FIG. 6, after passing through the Optical Element (OL), with non-radial symetry is of an elliptical-like shape in cross-section. FIG. 8b2 also can be taken to show that the spot shape looking down in FIG. 6, where the Electromagnetic Beam impinges on the Sample System (SS), (ie. at Point "D"), is essentially circular. Again, the oblique Angle-Of-Incidence causes elongation of the Electromagnetic Beam shape shown in FIG. 8c, so that at point "D" in FIG. 6 an essentially circular spot is achieved.

It is noted that the terminology "non-radial symetry" is used herein to identify an optical element with radial dimensions which are different in, for instance, orthogonal directions.

The terminology "outer annular region" as used herein is to be interpreted to mean an outer region of an electromagnetic beam, as distinct from a central region thereof, which outer region appears as an annulus when it is considered that the intensity of the beam decreases to zero as the radius increases to infinity. Said "outer annular region" can be considered to begin at the point where the intensity of an electromagnetic beam falls to where intensity becomes irregular rather than continues directly to zero. This often occurs at below approximately ten (10%) percent of maximum intensity, and it is noted, can contain approximately two (2%) to five (5%) of the electromagnetic beam's energy content.

It is also noted that the language "at least partially pass through" as regards an electromagnetic beam interaction with a pin hole (PH) in a diaphram, indicates that at least part of an electromagnetic beam, typically the central-most part, passes therethrough, with an annular region being blocked passage.

Finally, while technically a spatial filter (SF) is generally considered to consist of a converging lens or mirror, (or system of lens(es) and/or mirror(s)), an aperture and a collimating lens or mirror, (or system of lens(es) and/or mirror(s)), for the purposes of claim drafting it is to be understood that a spatial filter can be considered to further comprise such as a leading collimating lens and an aperture.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

What is claimed is:

1. A system which generates an electromagnetic beam and causes it to impinge upon a sample system (SS), said system comprising, prior to said sample system (SS), at least one spatial filter (SF) which serves to attenuate an outer annular region from said electromagnetic beam as it passes therethrough;

said system being further characterized by a selection from the group consisting of:

a) said at least one spatial filter (SF) is positioned prior to a beam directing reflecting means (PRI) for directing said electromagnetic beam, wherein said reflecting means (PRI) directs said electromagnetic beam toward said sample system (SS) along a pathway which is other than substantially direct from a source (LS) of said electromagnetic beam to said sample system (SS); and b) said electromagnetic beam is provided to said sample system (SS) through said at least one spatial filter (SF) along a substantially direct pathway from a source (LS) of said electromagnetic beam to said sample system (SS).

2. A system as in claim 1 in which said spatial filter (SF) sequentially comprises:

first beam collimating lens (L1);

aperture (A1);

aperture (A2);

beam converging at least one lens (SFL1) or mirror (SFM1);

diaphragm with a pin hole (PH) therein located essentially at the focal length of said at least one beam converging lens (SFL1) or mirror (SFM1); and second beam collimating at least one lens (SFL2) or mirror (SFM2);

such that in use the central portion of the electromagnetic beam which is collimated by said first beam collimating lens (L1) is caused to pass through said apertures (A1) and (A2), become focused on and at least partially pass through said pin hole (PH) in said diaphragm by said beam converging at least one lens (SFL1) or mirror (SFM1), and become recollimated by said second beam collimating at least one lens (SFL2) or mirror (SFM2).

3. A system as in claim 1 wherein the system is selected from the group consisting of:

reflectometer;

spectrophotometer;

ellipsometer;

spectroscopic ellipsometer;

polarimeter; and spectroscopic polarimeter;

and comprises said source (LS) of said electromagnetic beam in functional combination with said spatial filter (SF) which sequentially comprises:

beam converging at least one lens (SFL1) or mirror (SFM1);

diaphragm with a pin hole (PH) therein located essentially at the focal length of said beam converging at least one lens (SFL1) or mirror (SFM1); and beam collimating at least one lens (SFL2) or mirror (SFM2);

such that in use the electromagnetic beam is caused to become focused on and at least partially pass through said pin hole (PH) in said diaphragm by said beam converging at least one lens (SFL1) or mirror (SFM1), and then become recollimated by said beam collimating at least one lens (SFL2) or mirror (SFM2).

4. A system as in claim 1, in which the system comprises:
polarization state generator (PSG) which functionally includes said spatial filter (SF);
means for supporting said sample system (SS); and
polarization state detector (PSD).

5. A system as in claim 1, in which the spatial filter sequentially comprises:
aperture (A2);
first at least one lens SFL1 or mirror (SFM1);
pin hole (PH) containing diaphragm; and
second at least one lens (SFL2) or mirror (SFM2);
said pin hole (PH) containing diaphragm being positioned at the focal points of said first (SFL1) (SFM1) and second (SFL2) (SFM2) lenses or mirrors, such that a collimated electromagnetic beam from said aperture (A2) enters said first at least one lens (SFL1) or mirror (SFM1), is converged and at least partially passes through said pin hole (PH), and is re-collimated by said second at least one lens (SFL2) or mirror (SFM2).

6. A system as in claim 1 which sequentially comprises:
a. said source of electromagnetic beam (LS);
b. a polarizer element (P);
c. optionally a compensator element (C1);
d. optional additional element(s) (AC1);
e. said sample system (SS);
f. optional additional element(s) (AC2);
g. optionally a compensator element (C2);
h. an analyzer element (A); and
i. a detector system (DET);
wherein said spatial filter is present after said polarizer element but before said sample system, and sequentially comprises:
optional aperture (A2);
beam converging at least one lens (SFL1) or mirror (SFM1);
diaphragm with a pin hole (PH) therein located essentially at the focal length of said beam converging at least one lens (SFL1) or mirror (SFM1); and
beam collimating at least one lens (SFL2) or mirror (SFM2).

7. A system as in claim 1 which further comprises in functional combination with said spatial filter a means for effecting cross-sectional, essentially radially uniform energy density in said electromagnetic beams, said means for effecting cross-sectional, essentially radially uniform energy density in said electromagnetic beams comprising a sequential combination of:
optional beam expander (BE);
first beam collimator (BC1);
at least one multi-faceted optical element (MF1) (MF2);
beam condenser (BC); and
second beam collimator (BC2);
and being in a location selected from the group consisting of:
before said spatial filter; and
after said spatial filter.

8. A system as in claim 1 which further comprises an optical (OL) element with non-radial symmetry positioned prior to said sample system (SS) such that a spot caused thereupon by said electromagentic beam whereat it impinges, is substantially circular in shape.

9. A method of processing an electromagnetic beam to eliminate a radially outer annulus thereof, said method comprising placing at least one spatial filter(s) such that said electromagnetic beam passes therethrough, said spatial filter sequentially comprising:
aperture;
beam converging at least one lens or mirror;
diaphragm with a pin hole therein located essentially at the focal length of said beam converging at least one lens or mirror; and
beam collimating at least one lens or mirror;
such-that in use said electromagnetic beam which is caused to pass through said aperture, becomes focused on and at least partially passes through said pin hole in said diaphragm by said beam converging at least one lens or mirror, and becomes recollimated by said second at least one lens or mirror before being caused to proceed toward, and interact with, a sample system;
said method of processing being carried out in a system characterized by a selection from the group consisting of:
a) said at least one spatial filter is positioned prior to a beam directing reflecting means for directing said electromagnetic beam, wherein said reflecting means directs said electromagnetic beam toward said sample system along a pathway which is other than substantially direct from a source of said electromagnetic beam to said sample system; and
b) said electromagnetic beam is provided to said sample system along a substantially direct pathway from a source of said beam of electromagnetic radiation, through said at least one spatial filter to said sample system.

10. A method of processing an electromagnetic beams to eliminate a radially outer annulus thereof as in claim 9, in which the step of providing a spatial filter further involves providing a means for effecting cross-sectional, essentially radially uniform energy density in said electromagnetic beams comprising a sequential combination of:
optional beam expander;
first beam collimator;
at least one multi-faceted optical element;
beam condenser; and
second beam collimator;
in functional combination therewith, in a location selected from the group consisting of:
before said spatial filter; and
after said spatial filter.

11. A method of investigating a sample system, in the context of a system selection from the group consisting of:
reflectometer;
spectrophotometer;
ellipsometer;
spectroscopic ellipsometer;
polarimeter; and
spectroscopic polarimeter;
which causes an electromagnetic beam to interact with a sample system;
comprising the steps of:
a. providing an electromagentic beam;
b. providing said sample system;
c. placing at least one spatial filter(s) in the pathway of said electromagnetic beam such that said electromagnetic beam at least partially passes therethrough prior to said electromagnetic beam being caused to interact with said sample system; said system being characterized by a selection from the group consisting of:
a) said at least one spatial filter is positioned prior to a beam directing reflecting means for directing said electromagnetic beam, wherein said reflecting means directs said electromagnetic beam toward said sample system along a pathway which is other than substantially direct from a source of said electromagnetic beam to said sample system; and b) said electromagnetic beam is provided to said sample system along a substantially direct pathway from a source of said electromagnetic beam, through said at least one spatial filter to said sample system;

the purpose being to eliminate a radially outer annulus of said electromagnetic beam which is comprised of a low intensity level irregular content.

12. A method of investigating a sample system as in claim 11, in which the step of providing said at least one a spatial filter further involves providing a means for effecting cross-sectional, essentially radially uniform energy density in said electromagnetic beams comprising a sequential combination of:

optional beam expander;
first beam collimator;
at least one multi-faceted optical element;
beam condenser; and
second beam collimator;

in functional combination therewith, in a location selected from the group consisting of:
before said spatial filter; and
after said spatial filter.

13. A system selected from the group consisting of:
reflectometer;
spectrophotometer;
ellipsometer;
spectroscopic ellipsometer;
polarimeter; and
spectroscopic polarimeter;

which generates an electromagnetic beam and causes it to impinge upon a sample system, said system comprising, prior to said sample system, at least one spatial filter which serves to attenuate an outer annular region from said electromagnetic beam as it passes therethrough;

said system being characterized by a selection from the group consisting of:

a) said at least one spatial filter is positioned prior to a beam directing reflecting means for directing said electromagnetic beam, wherein said reflecting means directs said electromagnetic beam toward said sample system along a pathway which is other than substantially direct from a source of said electromagnetic beam to said sample system; and b) said electromagnetic beam is provided to said sample system along a substantially direct pathway from a source of said electromagnetic beam through said at least one spatial filter to said sample system.

14. A system as in claim 13 which further comprises a means for effecting cross-sectional, essentially radially uniform energy density in said electromagnetic beam, comprising a sequential combination of:

optional beam expander;
first beam collimator;
at least one multi-faceted optical element;
beam condenser; and
second beam collimator;

in functional combination with said spatial filter, in a location selected from the group consisting of:
before said spatial filter; and
after said spatial filter.

15. A system as in claim 13 which further comprises an optical (OL) element with non-radial symmetry positioned prior to said sample system (SS) such that a spot caused thereupon by said electromagnetic beam whereat it impinges, is substantially circular in shape.

16. A system comprising a source of a beam of electromagnetic radiation which generates an electromagnetic beam and causes it to impinge upon a sample system, said system comprising, prior to said sample system, at least one spatial filter which serves to attenuate an outer annular region from said electromagnetic beam as it passes therethrough;

said at least one spatial filter being positioned prior to a beam directing reflecting means for directing said electromagnetic beam, wherein said reflecting means directs said electromagnetic beam toward said sample system along a pathway which is other than substantially direct from said source of a beam of electromagnetic radiation to said sample system.

17. A system as in claim 16 which further comprises a means for effecting cross-sectional, essentially radially uniform energy density in said electromagnetic beams, comprising a sequential combination of:

optional beam expander;
first beam collimator;
at least one multi-faceted optical element;
beam condenser; and
second beam collimator;

in functional combination with said spatial filter, in a location selected from the group consisting of:
before said spatial filter; and
after said spatial filter.

18. A system as in claim 16 which further comprises an optical (OL) element with non-radial symmetry positioned prior to said sample system (SS) such that a spot caused thereupon by said beam of electromagnetic radiation whereat it impinges, is substantially circular in shape.

19. A system comprising a source of a beam of electromagnetic radiation which generates an electromagnetic beam and causes it to impinge upon a sample system, said system comprising, prior to said sample system, at least one spatial filter which serves to attenuate an outer annular region from said electromagnetic beam as it passes therethrough;

said system providing said electromagnetic beam to said sample system along a substantially direct pathway from said source of a beam of electromagnetic radiation to said sample system.

20. A system as in claim 19 which further comprises a means for effecting cross-sectional, essentially radially uniform energy density in said electromagnetic beams, comprising a sequential combination of:

optional beam expander;
first beam collimator;
at least one multi-faceted optical element;
beam condenser; and
second beam collimator;

in functional combination with said spatial filter, in a location selected from the group consisting of:
before said spatial filter; and
after said spatial filter.

21. A system as in claim 19 which further comprises-an optical (OL) element with non-radial symmetry positioned prior to said sample system (SS) such that a spot caused thereupon by said beam of electromagnetic radiation whereat it impinges, is substantially circular in shape.

* * * * *